United States Patent
Pratt et al.

(10) Patent No.: US 6,592,517 B2
(45) Date of Patent: *Jul. 15, 2003

(54) METHOD AND SYSTEM FOR PROVIDING ANIMAL HEALTH HISTORIES AND TRACKING INVENTORY OF RELATED DRUG USAGE

(75) Inventors: William C. Pratt, Canyon, TX (US); William D. McKillip, Amarillo, TX (US)

(73) Assignee: Micro Beef Technologies, Ltd., Amarillo, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/081,086

(22) Filed: Feb. 21, 2002

(65) Prior Publication Data

US 2002/0115915 A1 Aug. 22, 2002

Related U.S. Application Data

(62) Division of application No. 09/148,976, filed on Sep. 3, 1998, which is a division of application No. 08/226,292, filed on Apr. 11, 1994, now Pat. No. 5,803,906, which is a continuation of application No. 07/827,843, filed on Jan. 29, 1992, now Pat. No. 5,315,505, which is a continuation of application No. 07/457,388, filed on Dec. 27, 1989, now abandoned, which is a continuation of application No. 07/085,073, filed on Aug. 12, 1987, now abandoned.

(51) Int. Cl.$^7$ .............................. A61B 5/02; C06F 15/14

(52) U.S. Cl. ........................................ 600/300; 128/903

(58) Field of Search .................... 600/300; 128/903, 128/904, 898; 119/108

(56) References Cited

U.S. PATENT DOCUMENTS 3,626,377 A    12/1971  Markley
3,848,112 A    11/1974  Weichselbaum et al.
4,049,950 A     9/1977  Byrne et al.

(List continued on next page.)

FOREIGN PATENT DOCUMENTS

CA    1301329    5/1992

OTHER PUBLICATIONS

Shapiro, A., "SCAMP . . . ," *Proc Joint Conf. Soc. for Computer Medicine Soc. for Advanced Medical Systems*, Dec. 1981, R 858.A2 C6, pp. 51–54.

McEllhiney, R., "Micro Systems," *Feed Management*, vol. 38, No. 3, Mar. 1985, pp. 54–58.

Brimm, "Computers in Critical Care," *Critical Care Nursing Quarterly*, vol. 9, No. 4, Dec. 1987, pp. 53–63.

(List continued on next page.)

*Primary Examiner*—Samuel G. Gilbert
(74) *Attorney, Agent, or Firm*—Klarquist Sparkman, LLP

(57) ABSTRACT

A computer-based system for providing up-to-date health histories of animals, for example, in a feedlot. The system includes indicia means associated with each animal for identifying the animal and data entry means coupled to a computer for reading the indicia means to identify the animal to the computer. The data entry means also communicates to the computer treatment data comprising the animal's physical condition and any treatment administered to the animal. The computer is programmed to record the identity and associated treatment data and collect the data with previous data to provide the animal's health history. The system also displays the identified animal's prior health history at the animal's location for the operator's benefit, which location is typically an animal hospital remote from the computer's location. The system may include a second data entry means for determining the net amount of drugs taken for animal treatment from an inventory. The computer is programmed to compare the net amount taken against the amount administered in treatment as communicated by the first data entry means to determine a difference in the amounts.

105 Claims, 9 Drawing Sheets

U.S. PATENT DOCUMENTS

| | | | |
|---|---|---|---|
| 4,135,241 A | 1/1979 | Stanis et al. | |
| 4,288,856 A | 9/1981 | Linseth | |
| 4,290,114 A | 9/1981 | Sinay | |
| 4,336,589 A | 6/1982 | Smith et al. | |
| 4,360,125 A | 11/1982 | Martindale et al. | |
| 4,461,240 A | 7/1984 | Ostler | |
| 4,463,706 A | 8/1984 | Meister et al. | |
| 4,503,808 A | 3/1985 | McAlister | |
| 4,589,372 A | 5/1986 | Smith | |
| 4,604,847 A | 8/1986 | Moulding et al. | |
| 4,617,876 A | 10/1986 | Hayes | |
| 4,686,624 A | 8/1987 | Blum et al. | |
| 4,712,511 A | 12/1987 | Zamzow et al. | |
| 4,733,354 A | 3/1988 | Potter et al. | |
| 4,838,275 A | 6/1989 | Lee | |
| 4,839,806 A | 6/1989 | Goldfischer et al. | |
| 5,315,505 A | * 5/1994 | Pratt et al. | 600/300 |
| 5,499,626 A | 3/1996 | Willham et al. | |
| 5,803,906 A | * 9/1998 | Pratt et al. | 600/300 |
| 5,842,976 A | 12/1998 | Williamson | |

OTHER PUBLICATIONS

Alvin J. Edwards, D.V.M., Ph.D.; *The Personal Aspect of a Feedyard Health Program*; College of Veterinary Medicine, Kansas State University (Dec. 1980).

*Proceedings of International Conference on Veterinary Preventive Medicine and Animal Production; Australian Veterinary Journal*; Nov. 1985.

*Affidavit of Stephen W. Meyers*; United States District Court for the Northern District of Texas, Amarillo Division; Civ. No. 2:94–CV–293–J; Micro Chemical, Inc. v. Lextron, Inc. and Turnkey Computer Systems, Inc., May 1995.

*Online*, Monthly Newsletter from Turnkey Computer Systems, Inc., Customer Survey, Jun. 1986.

*Computer Application for the Food Animal Practitioner*, Bechtol & Jordah, Animal Health and Nutrition, Oct. 1985.

*Cattle Feedlot Health Management*, David T. Bechtol, B.S., D.V.M., Current Veterinary Therapy, Food Animal Practice, W.B. Saunders Company, Dec. 1981.

*Record Keeping: Key to Successful Feedlot Health Programs*, David T. Bechtol, D.V.M., Norden News, vol. 56, No. 1, Dec. 1981.

*Use of Computers in Cow–Calf Herd Management*, Garrett R. Oetzel, D.V.M., M.S., Robert G. Mortimer, D.V.M., M.S., The Bovine Proceedings, No. 18, Apr. 1986.

*Potential impact of on–farm microcomputers on livestock management and veterinary practice*, Anthony C. Bywater, Ph.D. and William J. Goodger, D.V.M., Ph.D., JAVMA, vol. 186, No. 3, Feb. 1, 1985.

*Wherefrom Good Hardware and Software?*, Steve Myers, Turnkey Computer Systems, Computer Management col. edited by B.J. Geiger, CALF News, vol. 24, No. 2, Feb. 1986.

*Clustering of fatal fibrinous pneumonia (shipping fever) in feedlot calves within transport truck and feedlot pen groups*, Carl S. Ribble, Mohamed M. Shoukri, Alan H. Meed, S. Wayne Martin, Preventive Veterinary Medicine 21, Dec. 1994.

*XIIIth World Congress on Diseases of Cattle*, Durban Republic of South Africa, World Buriatrics Association, Proceedings vol. I, Sep. 17–21, 1984.

*Fourteenth World Congress on Diseases of Cattle*, Dublin, Ireland, Aug. 26–29, 1986.

*So You're Looking for a Computer System*, Computer Management col. edited by B.J. Geiger, CALF News, vol. 23, No. 5, May 1985.

*Flyer announcing computer seminar*, Aug. 26 and 27, 1985.

*Attitudes and Expectations*, Steve Meyer, Turnkey Computer Systems, Computer Management col. edited by B.J. Geiger, CALF News, vol. 23, No. 7, Jul. 1985.

*Business and Fun at Seminar*, Champ Gross, West Coast Editor, CALF News, vol. 23, No. 10, Oct. 1985.

*Cattle, Computers and Financial Management*, Cal Siegfried and *The Search*, CALF News, vol. 24, No. 1, Jan. 1986.

*Managing Feedlot Operating Efficiency*, Chet Fields, Computer Management col. edited by B.J. Geiger, CALF News, vol. 24, No. 2, Mar. 1986.

*Making the Complex Simple*, Jeff Jackson, Computer Management col. edited by B.J. Geiger, CALF News, vol. 24, No. 4, Apr. 1986.

*AGNET: Serving the Cattle Industry for Over a Decade*, Computer Management col. edited by B.J. Geiger, CALF News, vol. 24, No. 5, May 1986.

*Computer Management* col. edited by B.J. Geiger, CALF News, vol. 23, No. 4, Apr. 1985.

*Texas Christian University advertisement*, CALF News, vol. 23, No. 3, Mar. 1985.

*The Computer Seminar—In Review*, Steve Dittmer, Midwest Editor, CALF News, vol. 21, No. 1, Jan. 1983.

*Important Attributes of a Computer System*, Jay O'Brien, CALF News, vol. 21, No. 4, Apr. 1983.

*Tools of the Trade*, Computer Management col. edited by B.J. Geiger, CALF News, vol. 23, No. 6, Jun. 1985.

*Chernobyl—Perhaps*, Computer Management col. edited by B.J. Geiger, CALF News, vol. 24, No. 8, Aug. 1986.

*Computer Judgments on the Feedlot*, CALF News, vol. 22, No. 8, Aug. 1984.

*Rough Draft of a Hospital Record Without Economic Considerations*, Aug. 12, 1986, Veterinary Research & Consulting Services.

*Applied Statistics and Computer Usage Related to Feedlot Animal Health*, Academy of Veterinary Consultants, Amarillo, Texas, Jun. 7, 1985.

*Herd Health—A Textbook of Health and Production Management of Agricultural Animals*, O.M. Radostits, D.V.M., M.Sc., D.C. Blood, O.B.E., M.V.Sc., W.B. Saunders Company, Dec. 1985.

*Safe, Effective and Legal Treatment Routines*, Dr. Al Edwards, Feedlot Management, Oct. 1980.

*Preventing Drug Problems in the Feedlot: A Guide for Managers and Veterinarians*, Alvin J. Edwards, D.V.M., Ph.D., The Bovine Practitioner—No. 16, Nov. 1981.

*Equipment for Farm Use in the National Cooperative Dairy Herd Improvement Program*, K.R. Butcher, North Carolina University and D.W. Webb, University of Florida, National Cooperative Dairy Herd Improvement Program, Dec. 1985.

*Date Finder/Schedulator*, Gjerstad Cattle Co., Copyright Dec. 1985.

*Feedlot Health Program*, Alvin J. Edwards, D.V.M., Ph.D., Dec. 1985.

*DHI Provo News*, Nov. 1985.

*The Software Catalog—Minicomputers* Dec. 1985.

*The Software Catalog—Microcomputers, Spring* Apr. 1984.

*The Information Aspect of Merchandising Your Feedlot*, Computer Management col. edited by B.J. Geiger, CALF News, vol. 23, No. 8, Aug. 1985.

*The Consultant's Role in Feedlot Practice*, Alvin J. Edwards, D.V.M., as presented to Eleventh Annual American Association of Bovine Practitioners, Baltimore, Maryland, Dec. 13, 1978.

*Seminar Speakers to Provide Valuable Insight*, CALF News (published prior to Aug. 1987).

*A Review of the Etiological Factors Associated with the Bovine Respiratory System*, Merwin Frey, D.V.M., Ph.D. Department of Veterinary Science, University of Nebraska, Lincoln, Apr. 1980.

*Computer User Confirms Value for Management Decisions*, CALF News, vol. 21, No. 8, Aug. 1983.

*Computer School Phase One*, Nov. 7–9 (published prior to Aug. 1987).

*Computer Assisted Management Operations Manual with Sample Printouts*, Dec. 1984.

*Computer, The Bovine Proceedings—No. 12*, Apr. 1980.

Norman, "Computing Animal Health Efficiency," *Department of Animal Science Cooperative Extension and California Cattle Feeders' Association California Feeder' Day Program*, pp. 16–20, Apr. 1, 1983.

Deposition of Michael Ray Boyd taken Dec. 13, 1994 (no exhibits).

Deposition of Donald L. Butler taken Dec. 12, 1994, including Exhibits 1 through 5.

Deposition of Alvin J. Edwards taken May 18–19, 1995, including Exhibits 3053 through 3062.

Deposition of William Jeffrey Hart taken Dec. 15, 1994, including Exhibits 169 through 181.

Deposition of William Jeffrey Hart taken Jan. 26, 1995, including Exhibits 1049 through 1051.

Deposition of Dr. Dee Griffin taken Jun. 14, 1999, including Exhibits 4137 and 165.

Deposition of Benny B. Norman, D.V.M., Ph.D., taken Feb. 10, 1999, including Exhibits 10000 through 10012.

Deposition of Benny B. Norman, D.V.M., Ph.D., taken Apr. 27, 1999.

Bechtol, D.V.M., *Good record–keeping system helps feeders avoid residue problems, The Drovers Journal Magazine*, section B, Jun. 1983.

Memo from Del Miles to David Owen regarding Hospital Computer Systems Dispute, dated Aug. 8, 1994, and referencing the outline dated Aug. 12, 1986.

Residue Avoidance Program Medication Withdrawal Calculator, prior to Sep. 3, 1998.

Geiger Deposition I, taken Mar. 14, 1989, pp. 14–16, 44, 71–72, 75, 78, 84, 102 and 105.

Geiger Deposition II, taken Nov. 16–17, 1994, pp. 26, 30, 76, 79, 86, 118, 122–123, 135, 178, 181–182, 223–224, and 254.

Animal Medical Records, by Turnkey Computers Systems, Inc., Amarillo, Texas, Jan. 1985 (cited by patent examiner in related '976 patent application).

\* cited by examiner

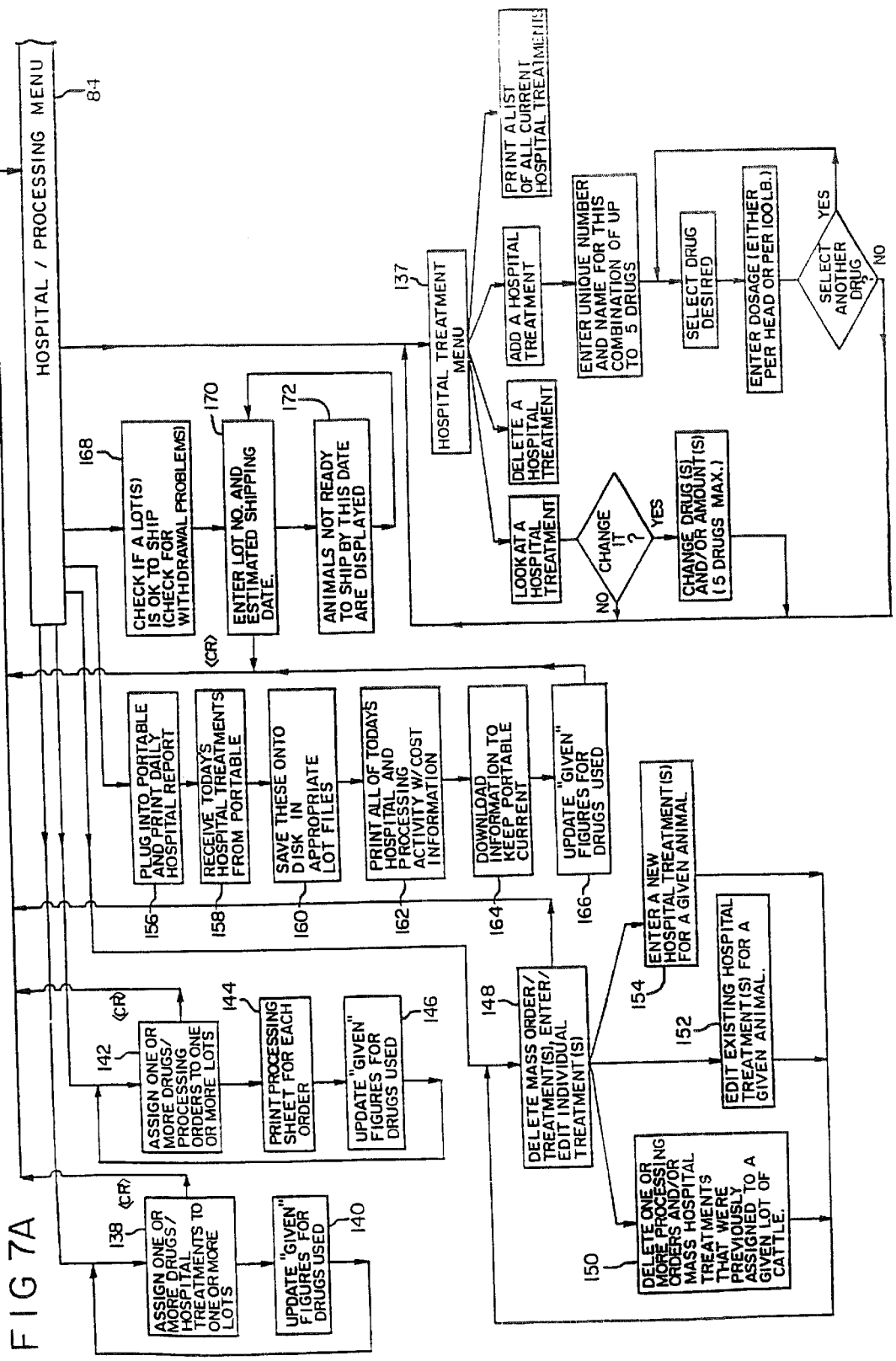

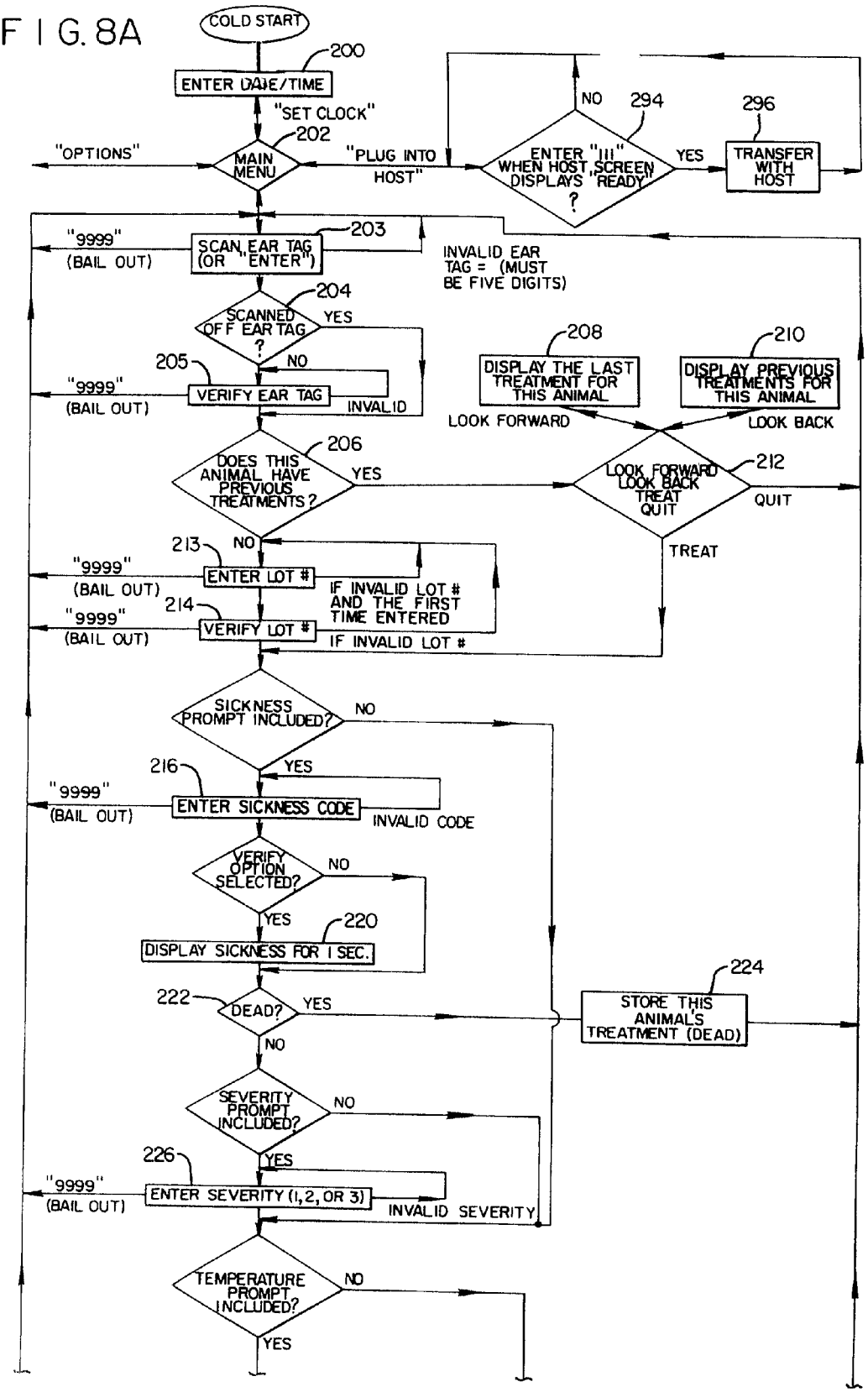

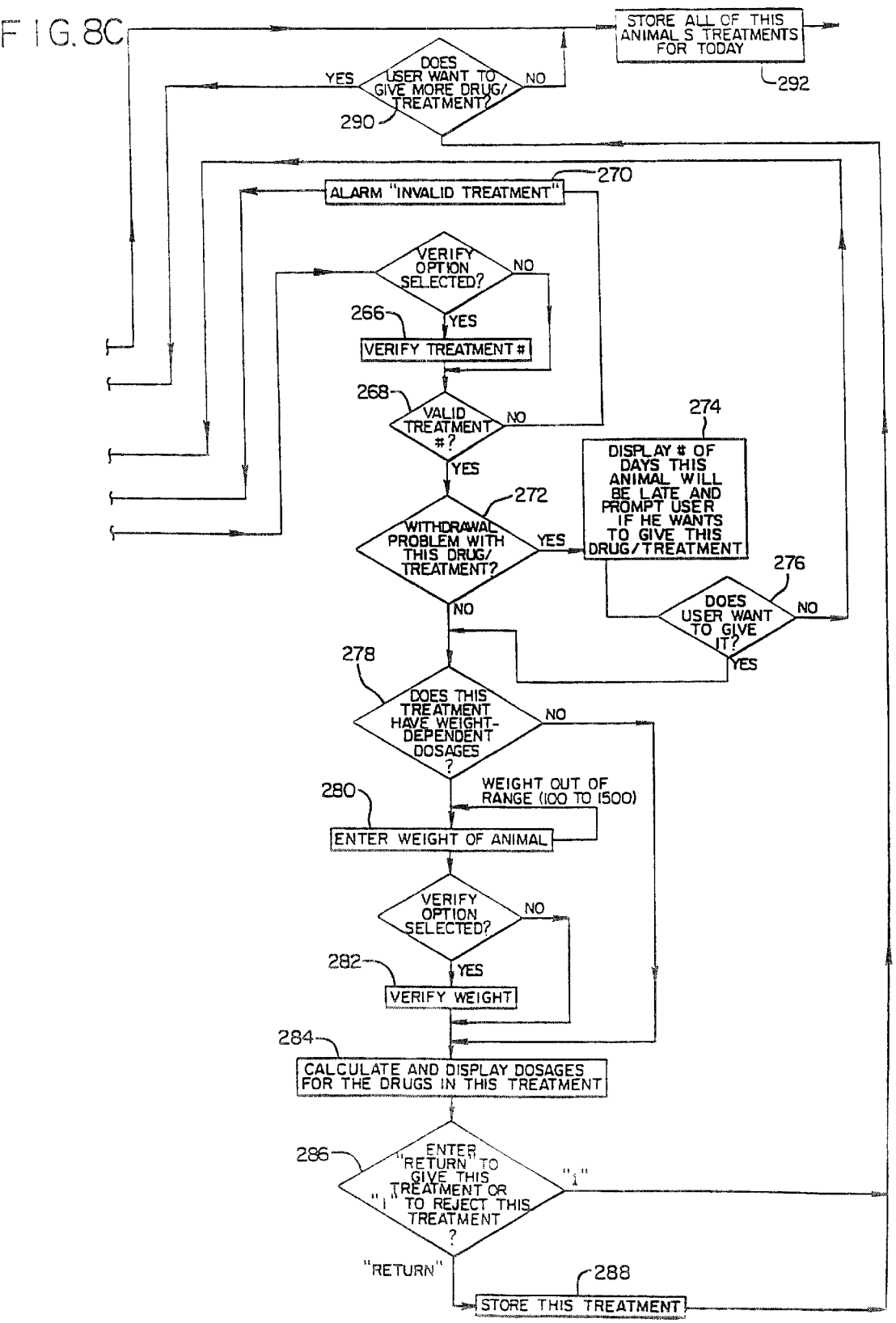

METHOD AND SYSTEM FOR PROVIDING ANIMAL HEALTH HISTORIES AND TRACKING INVENTORY OF RELATED DRUG USAGE

RELATED APPLICATION DATA

This is a divisional of application Ser. No. 09/148,976, filed Sep. 3, 1998, which is a divisional of application Ser. No. 08/226,292, now U.S. Pat. No. 5,803,906, filed Apr. 11, 1994, which is a continuation of application Ser. No. 07/827,843, filed Jan. 29, 1992, now U.S. Pat. No. 5,315,505, which is a continuation of application Ser. No. 07/457,338, filed Dec. 27, 1989, now abandoned, which is a continuation of application Ser. No. 07/085,073, filed Aug. 12, 1987, now abandoned.

BACKGROUND OF THE INVENTION

This invention relates generally to systems for providing individual health histories of animals, for example, in a cattle feedlot operation. More particularly, this invention relates to such a system wherein the identity of each animal and data representing the physical condition and treatment administered to each animal is recorded, made available at the animal's location, and accumulated with earlier data to provide an up-to-date health history of each animal.

Large scale cattle feedlot operations are commonly employed to feed cattle prior to slaughter. Typically, the cattle of a particular owner are identified by a lot number for keeping track of the goods and services provided for the cattle while in the care of the feedlot. Each individual head is further identified with a unique number such as by tag for keeping track of individual treatments required, such as drugs dispensed for each particular sickness, and for monitoring the physical condition of each animal. Through these identifying numbers, the feedlot operation can maintain a health history for each animal in each lot and charge the cattle owner for feed, drugs, and services provided for each head.

This system, although simple to implement, is slow and fraught with error because of the manual effort required to gather and record the data. Typically, data is manually recorded twice. At an animal hospital on the feedlot, cattle are observed and treated if necessary. An operator records in writing the physical condition of each animal, any observed sickness, and the drug treatment administered. This written record is then transferred to a clerk to be entered into a cumulative history. Both recordings are subject to error. Compounding the problem is the the potential for illegible entries, incomplete entries, and lost entries. For example, often cold, adverse weather conditions at a feedlot make it difficult for an operator to grip the pen for writing and also interfere with the flow of ink through the instrument. Moreover, the manual recording and rerecording are lengthy and consequently the cumulative health history is often several days out of date.

These problems associated with manual entry of data are well known, and attempts have been made to minimize the errors in several aspects of feedlot operations. For example, U.S. Pat. No. 4,288,856 to Linseth discloses an apparatus for separately feeding animals which have not gained sufficient weight. The Linseth apparatus is adapted to weigh each animal as it is walked through a weigh station. An operator reads the identification number that appears on an ear tag of the animal and enters the number into a keyboard connected to a computer. The animal is then weighed and the amount entered into the computer. The computer has stored within its memory different weight ranges for cattle, which the computer compares with the weight of the animal weighed. Each range is related to a gate that leads to a different feeding pen. The computer determines the weight range in which the animals lies and opens the appropriate gate to direct the animal to the desired feeding pen. The procdure is then repeated for reevaluation of the animal after a period of feeding. The Linseth apparatus, however, still requires manual entry of information and lacks any means for creating and displaying at the animal's location a cumulative history of the animal's physical condition and treatment administered.

Other apparatus have addressed individual monitoring of an animal's consumption. U.S. Pat. No. 4,461,240 to Ostler, for example, discloses a monitoring apparatus that dispenses a preselected amount of feed to a cow identified by a transmitter around its neck. The feeding station includes a receiver-transmitter in communication with a computer that has stored within its memory a feeding schedule for the animal. The computer determines how much feed is to be dispensed to each animal individually. The operator can thereby control how much each animal eats and monitor if in fact the prescribed amount of food is consumed. But the apparatus is limited in its ability to monitor and control the feeding of cattle.

U.S. Pat. No. 4,409,950 to Byrne et al. similarly discloses an animal food consumption monitor. Each animal bears a tag that includes a miniature transmitter which transmits a signal identifying the animal. The feed station for the animal includes a receiver for identifying the animal before it begins consuming feed. With the animal identified, the food in the station hopper is weighed before and then after the animal feeds to determine the amount consumed. The data on the amount and type of food consumed is then stored for later retrieval. The Byrne monitor, like the Ostler apparatus, identifies the animal without manual effort. But, again, it provides no on-site, up-to-date history of the animal's health.

Although the apparatus described above and others in the prior art offer some improvements in feedlot operations, they do not address the problem of maintaining up-to-date health histories of the physical condition and the drug treatment of the animals. Such histories are critical in determining the progress of a sick animal as well as keeping track of the cost of drugs for each animal. The manual method is thus still preferred for this purpose.

SUMMARY OF THE INVENTION

An object, therefore, of the invention is to provide an improved method and system for providing the health histories of animals.

Another object of the invention is to provide such a system which is portable to the animals' location.

Still another object of the invention is to provide such a system that avoids the need for manually identifying each animal to be treated and manually recording the physical condition and treatment administered.

Yet another object of the invention is to provide such a system that provides at the animals' location up-to-date health histories for each animal observed and treated by the system.

Yet another object of the invention is to provide such a system that compares the net amount of drugs taken for treatment from a drug inventory against the amount of drugs actually administered from the inventory to determine the difference in amounts.

To achieve these objects, a system according to the invention includes computer means for recording the identity of each animal and treatment data associated with the animal. This data comprises the physical condition of the animal and drug treatments administered to the animal. Each animal to be treated bears indicia means such as a bar coded ear tag or radio transmitter tag which can be read by data entry means such as a bar code scanner or antenna, respectively, to communicate the identity of the animal to the computer means. A bar coded menu sheet is also provided which can be read by the bar code scanner to communicate the treatment data associated with the animal at the time of treatment.

In one embodiment of the invention, the computer means comprises a host computer for storing the health histories of the animals and a portable unit for locating near an animal to be treated. The portable unit is adapted to record treatment data each time the animal is treated and to later transfer the data to the host computer for inclusion in the health history of the animal.

In a second embodiment of the invention, the computer means comprises a remote terminal connected directly to the host computer for transmitting data to the host computer without the need for recording and later transfer. This embodiment may be used where AC power is available.

The computer means may also track drug inventory for treatment of the animals and with a second data entry means for communicating to the computer means the removal and restocking of drugs from the inventory. The computer means is adapted to compare the net amount of drugs taken from the inventory as communicated by the second scanner against the amount of drugs used in treatment as communicated by the first scanner to determine a difference in the amounts.

In the method of the invention, a data terminal is provided at the location of the animal. An operator identifies the animal to the terminal, which displays the prior health history. If treatment is necessary, the operator enters data representing the drug treatment to be administered to the animal. Treatment data is then transferred to a host computer for accumulation with treatment data earlier recorded. The accumulated data comprises the health history of the animal. The updated history is then transferred from the host computer back to the data terminal.

The present invention eliminates the manual entry of this data and thus avoids the associated drawbacks of prior entry methods and systems.

The foregoing and other objects, features, and advantages of the invention will become more apparent from the following detailed description of a preferred embodiment which proceeds with reference to the accompanying drawings.

BRIEF DESCRIPTION OF THE DRAWINGS

FIG. 7A is a flowchart illustrating in more detail a portion of the hospital/processing menu within the programming of the host computer.

FIG. 8A is a flowchart illustrating a portion of the programming of the portable unit.

FIG. 8C is a flowchart illustrating a third portion of the programming of the portable unit.

DETAILED DESCRIPTION

The System—First Embodiment

Figure 1:
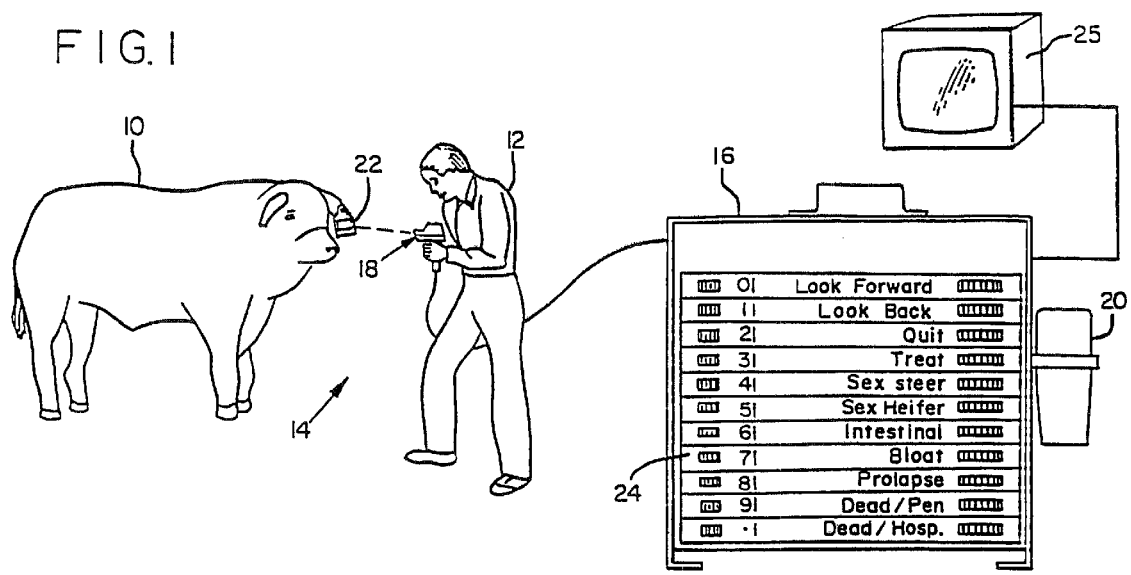
FIG. 1 is an illustration of a portable hospital unit included in a first embodiment of a system according to the invention.

Referring now to FIG. 1, there is shown an animal 10 and an operator 12 in an area of a cattle feedlot referred to as an animal hospital 14. An animal 10 may be brought to the hospital 14 for a check on its physical condition, for treatments that are administered to all animals in a particular lot, and if an animal is to be individually treated for sickness. Typically, the animal hospital 14 includes a cattle chute and a head gate (not shown) for holding the animal stationary while its weight and temperature are checked and any drugs are administered.

As indicated in FIG. 1, the system of the invention in this embodiment includes a portable hospital unit 16 that can be transported to the hospital 14 for use by the operator 12. This portability enables the operator to care for cattle with a single unit at several hospitals located around the feedlot rather than at a single hospital to which all cattle must be directed. Coupled to the portable unit 16 is a means for entering data into the unit such as an optical character reader, which in this first embodiment comprises a portable bar code scanner 18 available from a number of sources including the MSI Data Corporation under the name SYMBOLTEC LS8100. The scanner 18, which is stored in a holster 20 mounted to a side of the unit 16, is adapted to read indicia means such as an ear tag 22 bearing optical characters such as a bar code for uniquely identifying each animal. Rather than having to write down the animal's identifying number on a sheet, therefore, the operator 12 need only scan the ear tag 22 and the identifying number is electronically read and accurately recorded within the unit 16. The portable unit also includes a character menu sheet 24 that bears optical characters such as bar codes corresponding to treatment data comprising the observed physical condition of the animal as well as drug treatments that may be administered. The sheet 24 is mounted behind a clear plastic door of the unit 16 and includes bar codes on the sheet's left and right margins. The bar codes on the left margin are for entering identification numbers of drugs, numerical quantities, and menu selection steps during program execution. The bar codes on the right margin are for entering sickness codes, sex of the animal, and commands for scrolling through the prior health history, for entering data and for quitting after observation or treatment is concluded. The operator can thus enter the identity of the animal and treatment data by simply scanning the menu sheet 24 with the scanner 18. The treatment data is recorded along with the animal's identifying number within the unit 16. Visual feedback to the operator 12 of the prior health history and the data just entered is provided by a display device such as video monitor 25. The monitor 25 also displays the program prompts provided to the operator 12 by the unit 16 for entering the data, as will be described in detail hereafter.

Figure 2:
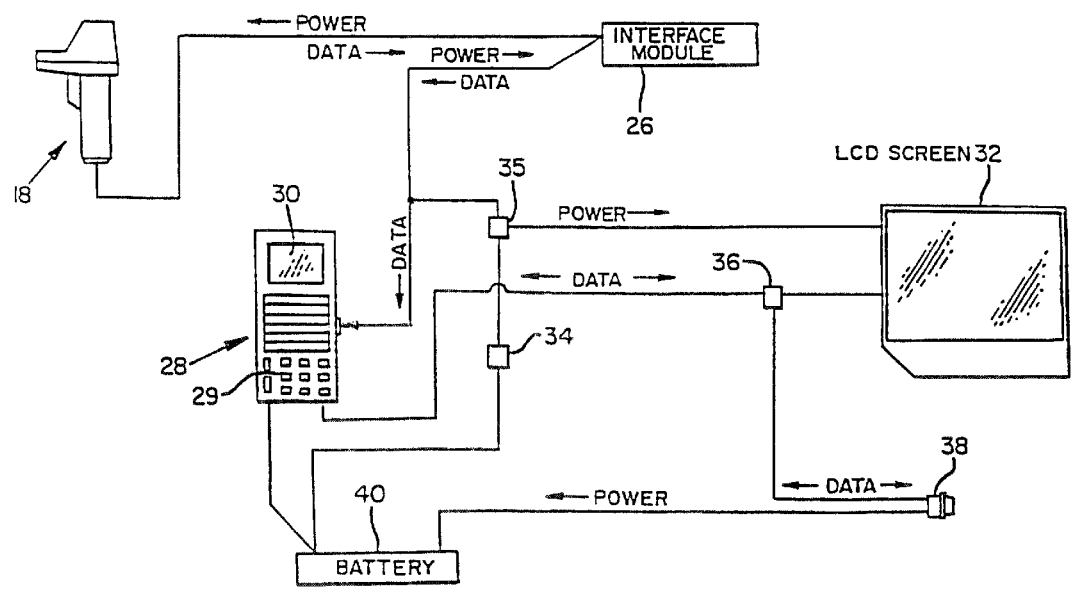
FIG. 2 is a schematic diagram of the portable hospital unit shown in FIG. 1.

FIG. 2 is a schematic diagram showing the elements within the chassis of the unit 16. The scanner 18 is connected via a spring cord to a conventional laser interface module 26 such as MSI Data Corporation Model 1365 for communicating data represented by optical characters to a portable terminal 28. The data terminal 28 is of conventional design such as a PDTIII available from the MSI Data Corporation and includes a microprocessor, associated memory for storing an instruction program and for recording data, a keyboard 29 for data entry, and a display 30 for displaying executing programs and recorded data. The keyboard 29 is reached through the door opening of the unit 16 and is an alternative to the scanner 18 for entering data that is not bar coded, such as the time and date of treatment and the lot number of the animal, or if the scanner malfunctions. Also shown in the schematic is an optional liquid crystal display (LCD) screen 32 connected to the terminal 28 through a reset switch 34, a power switch 35, and a selector switch 36. The reset switch 34 reinitializes the module 26. The switch 35 controls power to the scanner 18 and LCD screen 32 to electrically disconnect them when not required by the operator. The selector switch 36 directs the data that is entered via the scanner 18 into the terminal 28 to either the LCD screen 32 (visible through the transparent door of unit 16 above the menu sheet 24) or to the video monitor 25 via a serial data connector 38 such as an RS232 port. These additional display devices are optionally available because of the difficulty in reading the display 30 from a distance. The LCD screen 32 is normally selected by a single operator while the monitor 25 is usually employed when a crew is working in the hospital 14 and a number of the members must view the display simultaneously. The power source for the unit 16 is a battery 40 which is charged through a power supply line via the connector 38.

Figure 3:
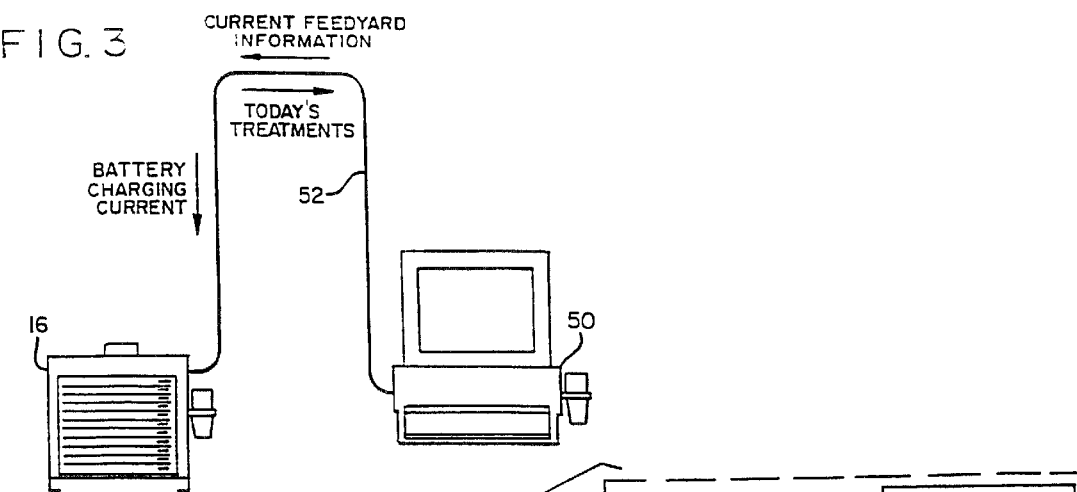
FIG. 3 is an illustration of the portable hospital unit in communication with a host computer included in the system.

Referring to FIG. 3, the data treatment recorded by the unit 16 is periodically transferred to a host computer 50 remote from the animal hospital 14 to update the health histories of observed and treated animals. The host computer 50 is intended for collecting data on feedlot operations in general and maintains the cumulative health history of each animal in the feedlot. The portable unit 16 when transferring the data is coupled to the host computer 50 via a conducting cable 52. The computer 50 in turn is adapted to collect the treatment data recorded within the portable unit 16 and produce an accumulation of such data associated with each animal. This accumulation of data comprises the animal's health history. After the current data is transferred, the computer 50 is programmed to transfer to unit 16 in return the up-to-date health history of each animal as well as current feedlot information, such as newly established lot numbers. The cable 52 also includes the power supply line for charging the battery 40 within the unit 16.

Figure 4:
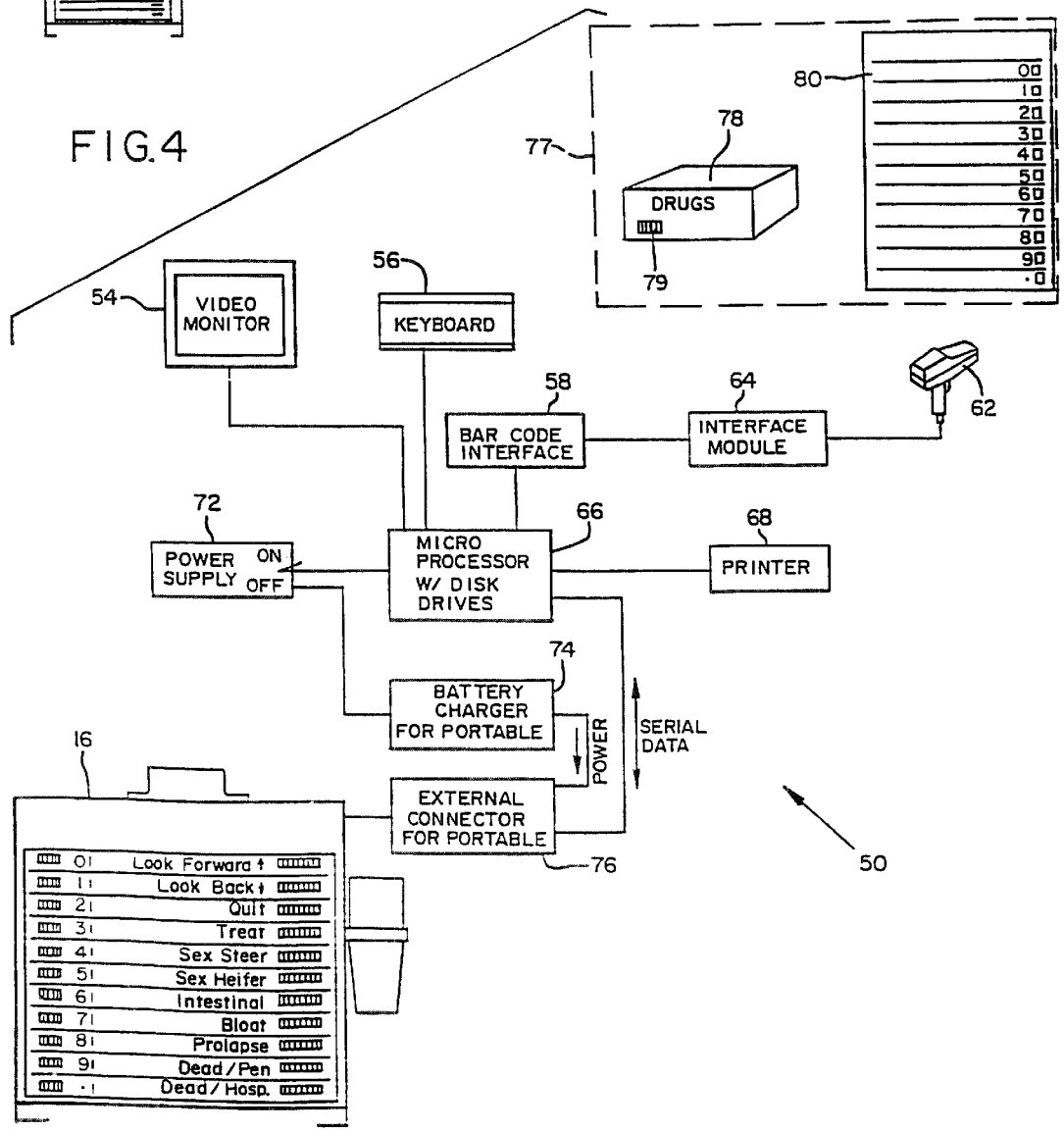
FIG. 4 is a schematic diagram of the animal health computer of FIG. 3.

FIG. 4 is a schematic diagram showing the elements comprising the computer 50. The computer itself is of conventional design and includes a video monitor 54 for displaying data and a keyboard 56 for data entry. The computer 50 includes an interface board 58 for receiving data entered via a second bar code scanner 62 and a second laser interface module 64. The interface board 58 transfers the data to and from a central microprocessor 66 equipped with internal memory and disk drives. Data and instruction programs stored in memory and on disk can be viewed on monitor 54. The computer 50 is also connected to a printer 68 for printing the health histories and other related documents. Power is supplied to the computer through a conventional power supply 72. The power supply 72 is also coupled to a battery charger 74 which supplies power for the unit 16. The up-to-date animal health histories, programming, and other feedlot information are transmitted as serial data from the computer 50 along with power to the unit 16 via a connector 76 coupled to the cable 52.

The host computer 50 serves a number of functions in addition to collecting treatment data to produce health histories for each animal treated. One related function is tracking inventory of drugs for treatment of the animals. Referring again to FIG. 4, computer 50 is located adjacent to a drug room 77 which stores drug inventory. Each drug container 78 is labeled with a bar code 79 for identifying the drugs therein and a menu sheet 80 is present for entering the amount of drugs within each container when removed for drug treatment and the amount remaining in each container when returned for restocking or when additional amounts are added to inventory. The computer 50 is programmed to compare the net amount of drugs taken from the inventory as communicated by the scanner 62 against the amount of drugs used in treatment in the animal hospital 14 as communicated by the scanner 18. The difference between the two amounts over a predetermined time can thereby be determined for monitoring loss due to breakage, theft, etc. This difference, as well as the comparable amounts, are printed at request as a drug usage report as will be described.

The System—Second Embodiment

Figure 5:
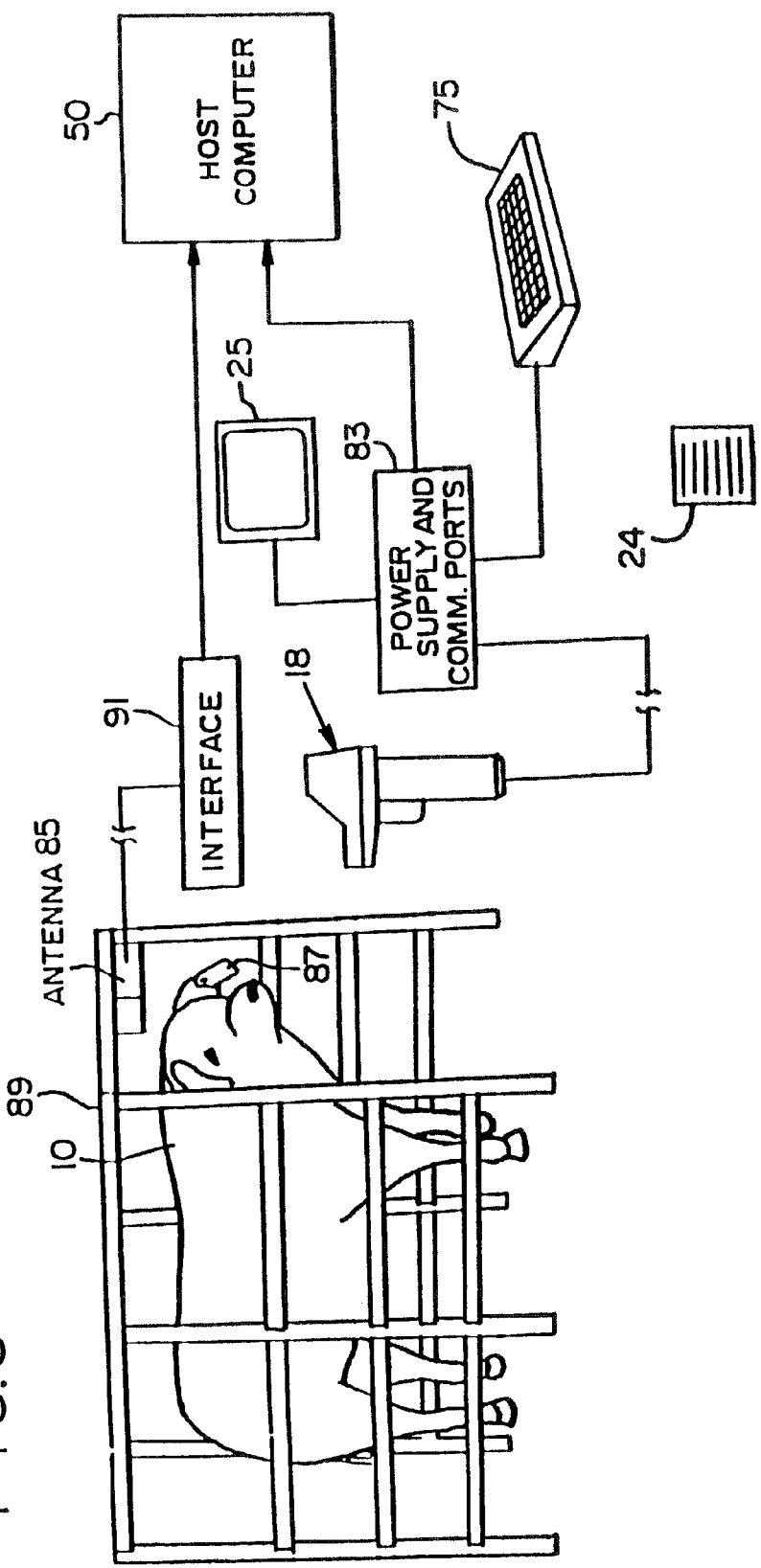
FIG. 5 is a schematic diagram of a second embodiment of the system according to the invention.

FIG. 5 shows a second embodiment of the system for possible use where a continuous source of power such as AC power is available in the hospital 14. The system includes a remote "dumb" terminal comprising the scanner 18, the video display 25, and a keyboard 75, all in communication with the host computer 50 through a node 83 that includes communication ports and a power supply. The terminal acts an extension of host computer 50, relaying treatment data to the computer in real time and displaying the up-to-date health histories transferred to the display from the host computer. This real time communication, when possible, avoids the need for physically moving the portable unit to the host computer and the delay in updating the prior health histories of the animals.

FIG. 5 also shows data entry means such as a transmitter-receiver antenna 85 and indicia means such as transponder 87 attached to an ear for identifying the animal 10. The antenna is preferably of a type similar to an RDREO1, integrater reader available from Allflex International and the tag is preferably a transponder of the type similar to an EID ear tag also available from Allflex International. The antenna is mounted along side the cattle chute 89 and emits a signal that reaches the transponder 87 when animal 10 passes by the antenna 85. The tag 87 in response emits a unique signal identifying the animal, which is electronically "read" by the antenna 87 and communicated to the host computer 50 via a computer interface unit 91 such as a CIUMO1 from Allflex International. Alternatively, the transponder 87 may be an active transmitter that continuously emits a radio signal for reception by a passive antenna 85. This means for automatically identifying the animal avoids the delay associated with the operator having to move to each animal for identifying it by scanning the ear tag. The entry of treatment data, however, is handled in the same manner as in the first embodiment, with the scanner 18 utilized to scan bar codes on menu sheet 24 corresponding to physical conditions and any drug treatment administered to the animal. The keyboard 75, however, is available if data cannot be entered via the antenna 85 or scanner 18.

METHOD OF OPERATION

Figure 6:
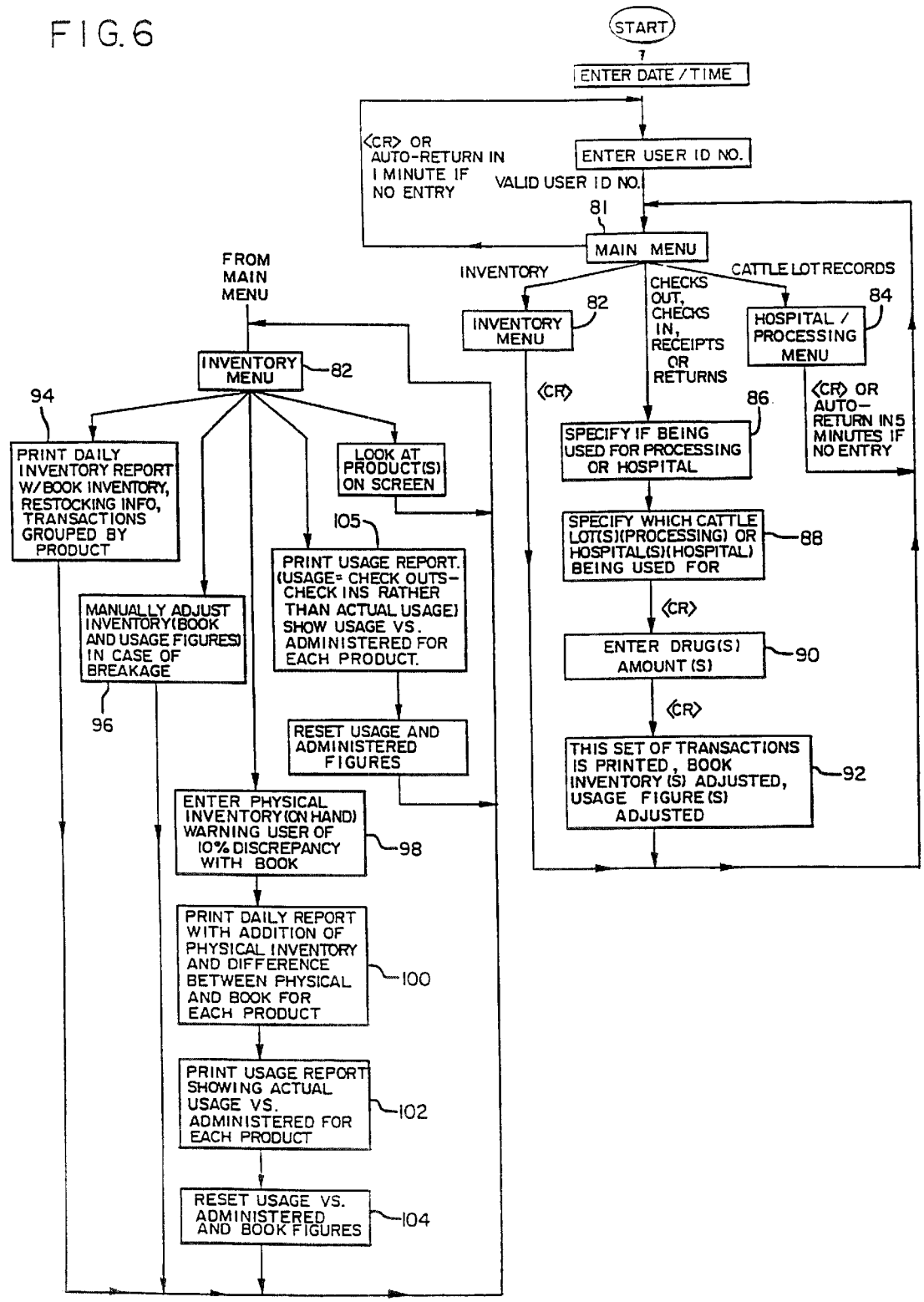
FIG. 6 is a flowchart illustrating the programming of the host computer.

The computer 50 and data terminal 28 within unit 16 are programmed in BASIC, according to the method illustrated in the flowcharts of FIGS. 6 through 8. FIG. 6 shows the options pertinent to the present invention and available to the operator upon logging onto the computer 50. A main menu (81) appears with three options. An inventory menu (82) is selected for working with the drug inventory; a hospital/processing menu (84) is selected for working with the cattle feedlot records; or the procedure for monitoring the removal and restocking of drugs is selected as drugs are to be used, such as in the animal hospital 14. With this third option, the operator scans the bar code 79 of the containers 78 that contain drugs required for treatment. He is then prompted to specify the purpose of the drug (86), specify the cattle lots the drug is being used for (88), and to enter the drug amounts removed and restocked (90). This data is used to adjust the book inventory stored within the computer's memory (92). The entry of data is indicated by "carriage returns" (CR).

The inventory menu option (82) is selected for monitoring the inventory. For example, one choice thereunder is to print the daily inventory report, with the book inventory, restocking information, and transactions grouped by product (94). Another option is to manually adjust the inventory in case of a breakage of drugs within the inventory (96). Other options include monitoring the difference between physical inventory as determined by a count and book inventory as determined by the checking in and checking out of drugs previously described. From the inventory menu (82), the operator can also enter the physical inventory for comparison against the book inventory (98). The difference between physical inventory and book inventory of each product (100) can then be presented. The actual physical usage as determined by a physical inventory of the drugs can be compared with the amount administered (102). The totals can then be adjusted as appropriate (104). The operator can additionally print the net amount taken from inventory for drug treatment against the amount recorded from the portable unit 16 (105) as administered.

Figure 7B:
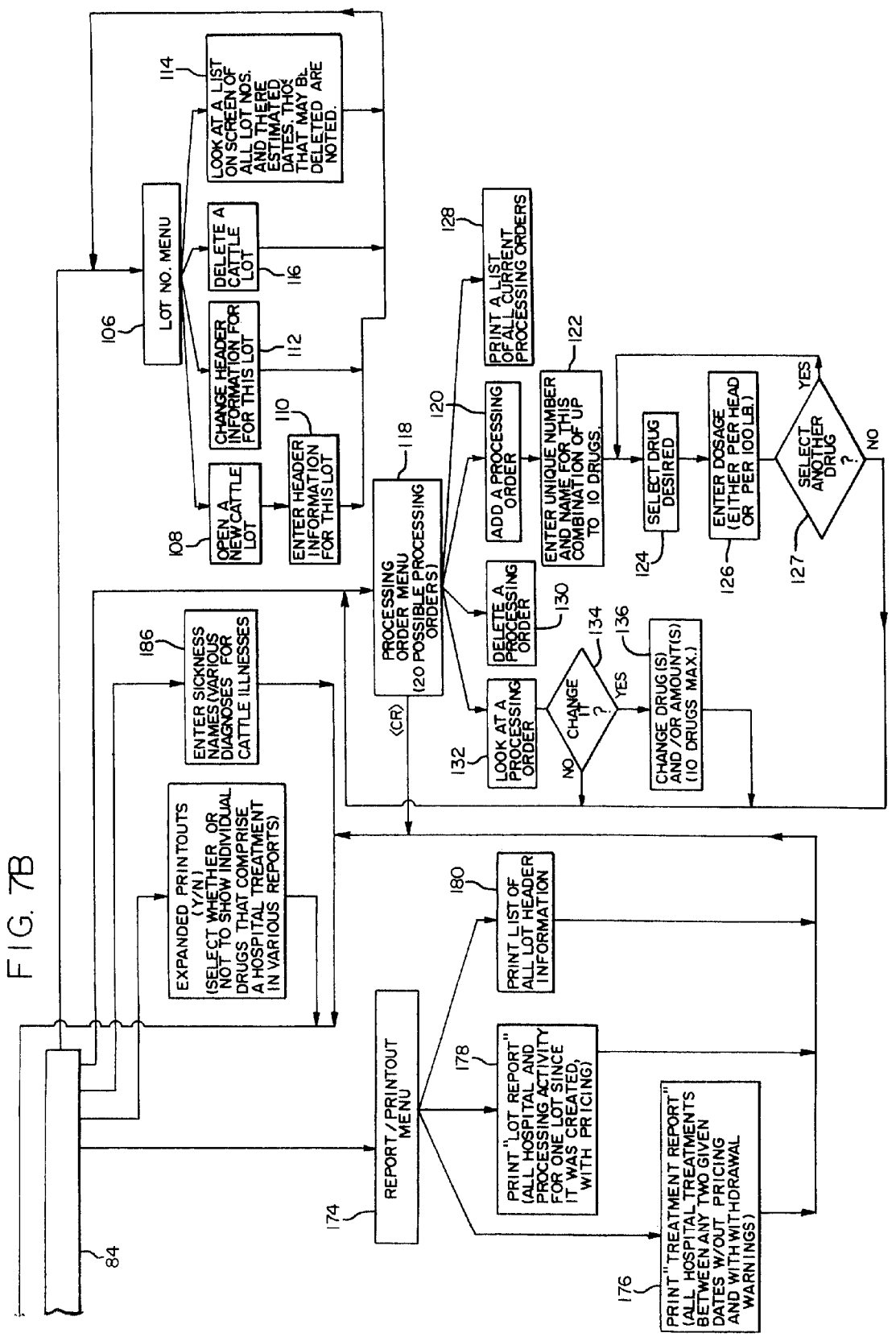
FIG. 7B is a flowchart illustrating in more detail a second portion of the hospital/processing menu within the programming of the host computer.

The third option of the main menu (81), the hospital/processing menu (84), enables the operator to set up new lots for cattle brought into the feedlot and to prepare group drug treatments known as processing orders and hospital treatments which are administered to the animals. Referring now to FIG. 7B, a first option is a lot number menu (106) appearing at the right of the figure and is selected whenever a new cattle lot is to be set up (108). This menu allows the operator to add header information to the lot (110), change the header information (112), or review the lots presently within the feedlot operation (114). The lot menu (106) also includes an option for deleting a cattle lot (116) after the cattle within the lot have been shipped from the feedlot.

A second option under the hospital processing menu is a processing order menu (118). Within this menu is a command for adding a processing order (120). First, a number is assigned to a unique combination of drugs to be administered as the processing order or treatment (122). The drugs desired are then selected (124), and the dosages per head or per 100 pounds are entered (126). The selection of drugs and dosages are then repeated until the processing order is complete (127). The menu (118) also permits the operator to print a list of current processing orders (128) or delete an existing processing order (130). An operator can also view a present processing order (132) and change it if desired (134) by changing the drugs or their amounts (136).

Referring now to FIG. 7A, a third option under the hospital/processing menu (84) is a hospital treatment menu (137). Hospital treatments differ from processing orders in that hospital treatments are normally intended for specific sicknesses and include a combination of drugs for treating that sickness. Processing orders, on the other hand, are not directed to specific sicknesses and are typically administered to all cattle in a lot, outside the animal hospital 14. The hospital treatment menu (137) includes basically the same selections as in the processing order menu (118) and for brevity descriptions of the selections therein are not repeated here.

The other options under the hospital/processing menu (84) include an option (138) at the left of FIG. 7A enabling the operator to assign and record treatments for the animals without entering the data through the portable unit 16. This option minimizes data entry where it is known that all cattle in a given lot will receive a specified treatment. The option (138) includes a command for updating the figures for drugs used in each hospital treatment (140). A similar option (142) allows the operator to assign one or more drugs or processing orders to one or more lots. The operator can print the processing sheet for each order (144) and also has the ability to update figures in the orders for the drugs used (146).

Just as he can assign drugs and treatments to lots, the operator has the option of deleting and editing treatments (148). These options include deleting previously assigned treatments (150), editing existing treatments for a given animal (152), and entering new hospital treatments for a given animal (154).

Communication via cable 52 with the portable unit 16 is also handled through the hospital/processing menu (84). The menu (84) allows the operator to print the daily hospital report (156) of the animals treated as well as receive the day's hospital treatment from the portable (158). The daily treatments are stored on disk in appropriate lot files (160). The operator can also print the day's hospital and processing activity with cost information (162). The updated health history and new lot numbers are then be downloaded into the portable unit 16 to keep it current (164). The program also updates in memory the amount of drugs used in treating each animal (166).

One concern of feedlots is the shipping of cattle not yet suitable for consumption. A further option under the menu (84) allows the operator to check when a lot may be shipped (168) by entering the lot number and estimated shipping date (170). Animals that are not ready for shipping within the lot are then displayed by number (172).

Referring again to FIG. 7B, an operator selects the report/printout menu option (174) whenever a report on treatments administered for each lot is required. Under menu (174), an operator can print a treatment report which indicates all hospital treatments between any two given dates (176). The operator may also print the lot reports which indicate all treatment with drug cost, both processing and hospital, administered to a specified lot since a lot was created (178). A third selection is for summarizing information on each lot by simply printing the header (180).

One other option shown allows the operator under menu (84) to enter the sickness names such as bloat, prolapse, etc., that will be recognized by the portable unit 16 and will appear on menu sheet 24 (186). If the sickness codes are changed at the hospital/processing menu, the menu sheet 24 is also updated.

Figure 8B:
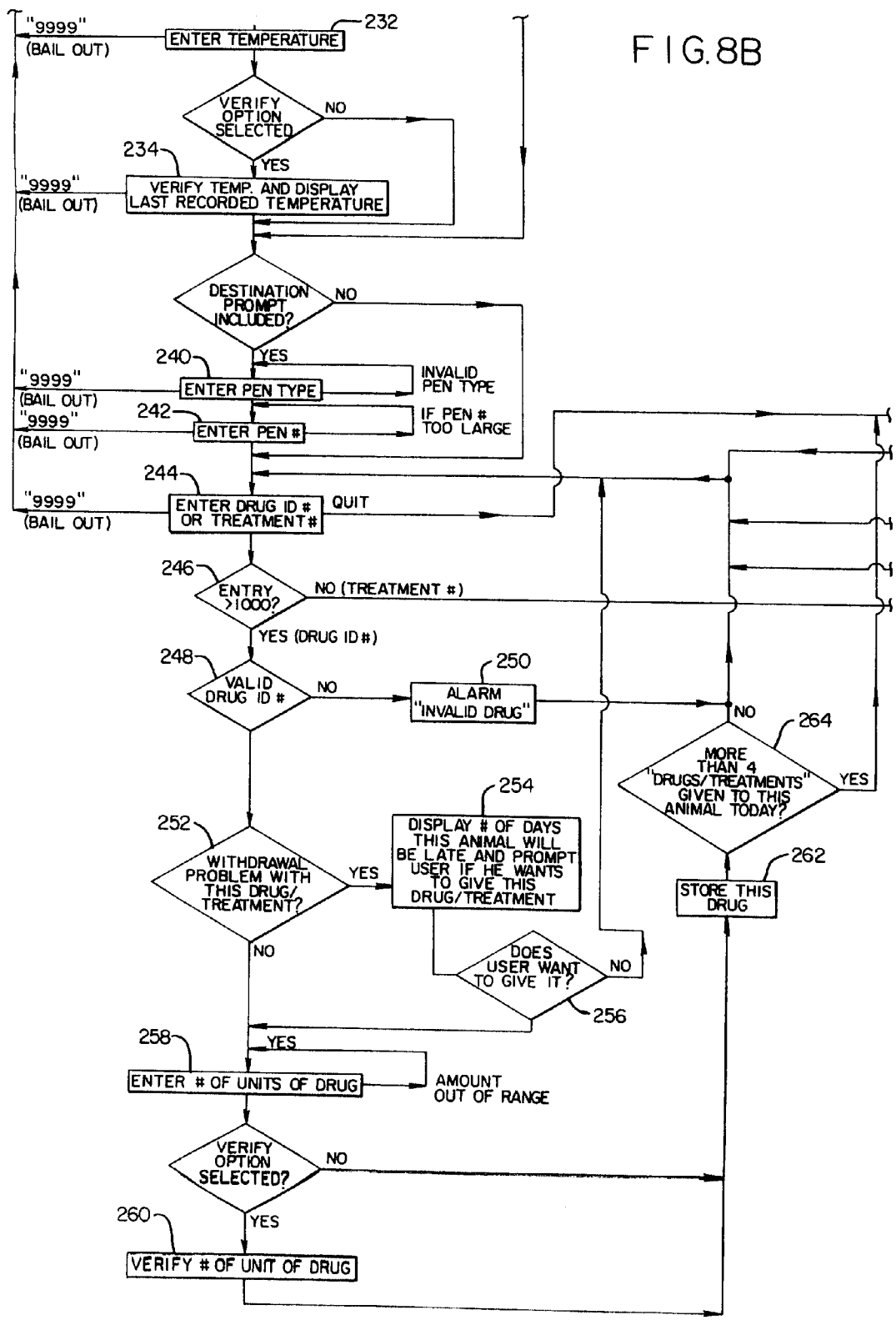
FIG. 8B is a flowchart illustrating a second portion of the programming of the portable unit.

The treatment data recorded in the portable unit 16 during a treatment session is entered in response to prompts from the instructional program stored within the terminal 28. FIGS. 8A–8C illustrate the operation of this program. Referring to FIG. 8A, the program prompts the operator 12 on the display such as video monitor 25 to enter the date and time of treatment via the keyboard 29 (200). A main menu (202) then appears on the monitor 25, which gives the operator several choices. One choice allows the operator to include and exclude various prompts and verifications of entered data which appear throughout the figure. Deletion of verifications, shown in these flowcharts, may be made by experienced operators who known the program operation well. The second choice commands the unit 16 to transfer its data to the host computer 50. A third choice allows for the entry of treatment data initially.

The operator thus begins treatment with this third choice by scanning the appropriate number on the menu sheet 24. He is then prompted to scan the ear tag of the animal to be treated or key in the tag number to identify the animal to the unit 16 (203). If he scans the tag, the number is automatically verified (204). If keyed in, the ear tag number is then displayed so that the operator may visually verify his entry (205) before scanning a CR. Once the ear tag has been verified, the program checks to see if the animal is new or has a previous treatment history (206). If the animal does have a record, the monitor 25 displays the last treatment for the animal (208). The operator can then scroll through previous treatments (210) via commands on menu sheet 24 to determine the health history of the animal (212). The operator can also quit the program by scanning the quit command on the menu sheet 24. The quit option is always available throughout the program, though not repeatedly shown in the figure for clarity. All data entered before the quit command is invoked is recorded. On the other hand, the operator can always "bail out" of the program if trouble develops therein by scanning the numerals 9999. No data entered during a treatment session is saved if the operator "bails out."

If no previous treatments have been administered, the operator enters the lot number through keyboard 29 (213) and scans the CR. The program then compares the lot number with those stored in memory. If it is a new lot number, the program alerts the operator that it is included and prompts for reentry. Entering the same number a second time establishes the lot number. The program then prompts the operator to verify his entry (214), which he does by a CR scan.

The operator is then prompted to enter a sickness code (216), such as a respiratory or intestinal condition, appearing on the menu sheet 24. The code is then displayed momentarily for the operator's verification (220). If the sickness code entered indicates the animal is dead (222), this data is stored immediately (224) and the treatment session is ended. If the animal is merely sick, however, the operator is prompted for the severity of the illness and enters a severity code number in response such as 1, 2, or 3 (226) from the menu sheet 24.

Following entry of the animal's identity and sickness diagnosis, the operator may be prompted for other physical conditions such as the animal's temperature. Referring to FIG. 8B, he enters the temperature (232) in response, and it is displayed by the program for operator verification. The last recorded temerature is also displayed (234). The program then prompts the operator for the animal's destination, and the operator enters the pen type and particular pen number by scanning the corresponding numbers on the menu screen 24 (240, 242). These pen types include home pens, recovery pens, or hospital pens such as hospital 14.

Following the intended destination, the operator is prompted to enter numbers identifying the drug or hospital treatment to be administered to the animal (244). Each individual drug and hospital treatment has a unique identification number. If the number entered by the operator is greater than 1000, i.e., has four digits, then the program determines that an individual drug is to be administered (246). The identification number is then checked against a stored list to determine if it is valid (248). The operator is alerted if the number is invalid, and he may attempt reentry (250). Once a valid identification number has been entered, the program checks to determine if the drug requires a withdrawal date (252). Certain drugs require that the animal be kept in the feedlot for a period of time after it is administered a drug to prevent undesired side effects to consumers. The program has stored within it the time period for each drug and calculates from the treatment data the earliest release date of the animal thereafter. If the drug has a withdrawal problem, the information is displayed (254) and the operator is given the opportunity to reconsider administering the drug (256). If no withdrawal date is displayed or if the operator chooses to administer the drug in any event, the program then prompts the operator to enter the number of units to be administered (258). The amount entered is checked against an allowable dosage range to protect the animal from an overdose. The portable unit 16 then verifies the number of units to be administered (260). This drug treatment data is stored within the memory of the terminal 28 for later transfer to the computer 50 (262). The operator is then queried if more treatments are to be given the animal in the present treatment session (264).

Administering and recording hospital treatments are similar to the steps followed for individual drugs. Returning to step (246) and then referring to FIG. 8C, an entered number less than 1000, i.e., two digits, is first verified by the operator as a hospital treatment number (266) via a scanned CR. The program then checks to see if the number entered is a valid treatment number (268). The operator is alerted if the number is invalid (270). If the number is valid, the program then determines if there is a withdrawal problem with this treatment (272) and displays the appropriate information if such problem exists (274). The operator again has the option to proceed or choose another treatment or drug (276). The program also determines whether the treatment has a weight dependent dosage (278). If so, the program prompts the operator to enter the animal's weight (280), which must fall within a predetermined range to be accepted as valid. The entered weight is then verified by the operator (282) via a scanned CR, and the program calculates and displays the dosages to be administered (284). The operator at this point can accept or reject the treatment as calculated (286). If accepted and administered, the amount of treatment is then stored (288).

The operator is then prompted to determine if further drugs or treatment is to be administered to the particular animal (290) in this treatment session. If treatment is finished, all data is then stored within the memory of the terminal 28 and the operator proceeds to examine the next animal. Once treatment is concluded, the operator quits the program (292).

At the conclusion of the day or other predetermined reporting period, the unit 16 is carried to the location of the computer 50 and the two connected by cable 52. Referring again to FIG. 8A, the operator then initiates data transfer via the main menu of the program within the unit 16 (202). The appropriate commands are first selected on the host computer 50 (156–160). The operator then enters a transfer command in response to a prompt (294), and the data is transferred (296). The transferred data is collected to update the health histories of the animals treated in that session. The updated health histories are then transferred back to the terminal 28 for review and display in steps (208) through (212).

Where the "dumb" terminal is employed in place of the portable unit 16, the instructional program illustrated in FIGS. 8A–C is stored within the memory of the host computer 50. No recording of data for later transfer, however, is required.

Having illustrated and described the principles of the invention in a preferred embodiment, it should be apparent to those skilled in the art that the invention can be modified in arrangement and detail without departing from such principles. For example, although the invention is described in the context of a feedlot, it is not so limited. I claim all modifications coming within the spirit and scope of the following claims.

I claim:

1. A method of assisting an operator in selecting and deciding whether to administer a selected drug treatment to animals which are selected from a group of retained animals for treatment at a drug treatment location, the method comprising:

storing in a computer health and drug treatment histories of animals to be treated;

entering into the computer the identity of an animal to be treated at the drug treatment location;

in response to entry of the animal's identity, providing through the computer at the drug treatment location the animal's health and drug treatment history, the history including prior diagnoses and drug treatments;

diagnosing the animal to be treated;

entering the diagnosis into the computer;

storing the diagnosis in the computer as an addition to the animal's health history;

evaluating the animal's health and drug treatment history and the animal's diagnosis;

storing in the computer a list of available drug treatments and their drug withdrawal periods;

providing through the computer to an operator at the drug treatment location a list of available drug treatments;

based at least in part on the evaluation of the animal's health and drug treatment history and the animal's diagnosis, the operator selecting a drug treatment for the animal from the list of drug treatments;

entering the selected drug treatment into the computer;

following entry of the selected drug treatment, providing through the computer to the operator at the drug treatment location drug withdrawal information that includes or is derived from a drug withdrawal period;

determining from the drug withdrawal information whether to administer the drug treatment;

if desired, administering the selected drug treatment to the animal; and storing any administered drug treatment in the computer as an addition to the animal's drug treatment history.

2. The method of claim 1 wherein the withdrawal information is a drug withdrawal period.

3. The method of claim 1 wherein the withdrawal information includes an animal shipping date and animal treatment date.

4. The method of claim 1 wherein the withdrawal information includes the number of days the animal will be late for shipping if the drug is administered.

5. The method of claim 1 wherein the withdrawal information includes a calculated earliest release date for the animal.

6. The method of claim 1 wherein the drug treatment history provided by the computer at the drug treatment location includes treatment cost.

7. The method of claim 6 including comparing through the computer an amount of drugs used in administering selected drug treatments against an amount of drugs taken from inventory for use in such treatments.

8. The method of claim 1 wherein entering into the computer the identity of an animal to be treated at the drug treatment location includes electronically identifying the animal to the computer.

9. The method of claim 1 wherein providing through the computer at the drug treatment location withdrawal information for the selected drug treatment includes displaying the number of days the animal will be late for shipping if the drug is administered and prompting an operator to determine if the operator wants to give the drug treatment.

10. The method of claim 1 including providing through the computer a list of animals and associated shipping status based on drug withdrawal information.

11. The method of claim 1 wherein providing through the computer at the drug treatment location withdrawal information for the selected drug treatment includes calculating in the computer when the animal may be released.

12. The method of claim 1 wherein providing through the computer at the drug treatment location withdrawal information for the selected drug treatment includes calculating in the computer an earliest permitted release date related to a drug withdrawal period and comparing that date with a date the animal is scheduled to be shipped.

13. The method of claim 12 including alerting the operator if the release date is later than the shipping date.

14. The method of claim 1 wherein said providing through the computer at the drug treatment location, the animal's drug treatment history includes providing prior drug treatments administered between two given dates.

15. The method of claim 1 including, in response to entry of an estimated shipping date for a group of animals, indicating whether the group is safe to ship based on the drug withdrawal information for animals within the group.

16. The method of claim 1 including, in response to entry of a lot number for a group of animals, indicating whether the group is safe to ship based on the drug withdrawal information for animals within the group.

17. The method of claim 1 including, in response to entry of pen number for a group of animals, indicating whether the group is safe to ship based on the drug withdrawal information for animals within the group.

18. The method of claim 1 including entering an animal weight and, following entry of the selected drug treatment, providing through the computer to the operator at the drug treatment location a weight-dependent dosage.

19. The method of claim 18 including alerting the operator if the entered animal weight is outside an allowable range.

20. The method of claim 1 including, in response to entry of the selected drug treatment:

providing through the computer a prompt to an operator to enter into the computer a dosage of drugs to be administered; and alerting the operator through the computer if the entered dosage is outside an allowable range.

21. The method of claim 1 wherein entering the diagnosis into the computer includes electronically entering sickness codes.

22. The method of claim 1 wherein entering the diagnosis into the computer includes electronically entering a temperature for the animal.

23. The method of claim 1 including entering into the computer a destination for the animal after its treatment.

24. The method of claim 1 including alerting an operator, after the entering of the selected drug treatment into the computer, whether the selected drug treatment is invalid.

25. The method of claim 1 including alerting the operator if the drug treatment being administered will affect the release date of the animal.

26. The method of claim 1 wherein providing through the computer at the drug treatment location withdrawal information for the selected drug treatment includes displaying the drug withdrawal period.

27. A method of assisting an operator in selecting and deciding whether to administer a selected drug treatment to animals which are selected from a group of retained animals for treatment at a drug treatment location, the method comprising:

storing in a computer health and drug treatment histories of animals to be treated;

entering into the computer the identity of an animal to be treated at the drug treatment location;

in response to entry of the animal's identity, providing through the computer at the drug treatment location the animal's health and drug treatment history, the history including prior diagnoses and drug treatments;

diagnosing the animal to be treated;

entering the diagnosis into the computer;

storing the diagnosis in the computer as an addition to the animal's health history;

evaluating the animal's health and drug treatment history and the animal's diagnosis;

storing in the computer a list of available drug treatments and their drug withdrawal periods;

providing through the computer to an operator at the drug treatment location a list of available drug treatments;

based at least in part on the evaluation of the animal's health and drug treatment history and the animal's diagnosis, the operator selecting a drug treatment for the animal from the list of drug treatments;

entering the selected drug treatment into the computer;

following entry of the selected drug treatment, alerting an operator with drug withdrawal information that includes or is derived from a drug withdrawal period;

if desired, administering the selected drug treatment to the animal; and storing any administered drug treatment in the computer as an addition to the animal's drug treatment history.

28. The method of claim 27 wherein the operator is alerted at the drug treatment location.

29. The method of claim 27 including entering an animal weight and, following entry of the selected drug treatment, providing through the computer to the operator at the drug treatment location a weight-dependent dosage.

30. The method of claim 27 wherein the withdrawal information is a drug withdrawal period.

31. The method of claim 27 wherein the withdrawal includes an animal shipping date and animal treatment date.

32. The method of claim 27 wherein the withdrawal includes the number of days the animal will be late for shipping if the drug is administered.

33. The method of claim 27 wherein the withdrawal includes a calculated earliest release date for the animal.

34. The method of claim 27 including alerting an operator if the animal weight is outside an allowable range.

35. The method of claim 27 including alerting an operator if the dosage of drugs to be administered is outside an allowable range.

36. The method of claim 27 including alerting the operator if the drug treatment being administered will affect the release date of the animal.

37. The method of claim 27 wherein alerting an operator with drug withdrawal information for the selected drug treatment includes displaying the drug withdrawal period.

38. The method of claim 37 wherein entering into the computer the identity of an animal to be treated includes electronically identifying the animal to the computer.

39. The method of claim 27 wherein entering into the computer the identity of an animal to be treated includes electronically identifying the animal to the computer.

40. A method of assisting an operator in selecting and deciding whether to administer a selected drug treatment to animals which are selected from a group of retained animals for treatment at a drug treatment location, the method comprising:

storing in a computer health and drug treatment histories of animals to be treated;

entering into the computer the identity of an animal to be treated at the drug treatment location;

in response to entry of the animal's identity, providing through the computer at the drug treatment location the animal's health and drug treatment history, the history including prior diagnoses and drug treatments;

diagnosing the animal to be treated;

entering the diagnosis into the computer;

storing the diagnosis in the computer as an addition to the animal's health history;

evaluating the animal's health and drug treatment history and the animal's diagnosis;

storing in the computer a list of available drug treatments and their drug withdrawal periods;

providing through the computer to an operator at the drug treatment location a list of available drug treatments;

based at least in part on the evaluation of the animal's health and drug treatment history and the animal's diagnosis, the operator selecting a drug treatment for the animal from the list of drug treatments;

entering the selected drug treatment into the computer;

following entry of the selected drug treatment, providing through the computer to the operator at the drug treatment location drug withdrawal information that includes or is derived from a drug withdrawal period;

if desired, administering the selected drug treatment to the animal;

storing any administered drug treatment in the computer as an addition to the animal's drug treatment history; and prior to shipping the animal, providing through the computer to an operator at the animal's location drug withdrawal information that includes or is derived from a drug withdrawal period.

41. The method of claim 40 including the operator determining from the drug withdrawal information whether sufficient time has passed since administering the drug treatment to ship the animal.

42. The method of claim 41 wherein the withdrawal information is a drug withdrawal period.

43. The method of claim 41 wherein the withdrawal information includes an animal shipping date and animal treatment date.

44. The method of claim 41 wherein the withdrawal information includes the number of days the animal will be late for shipping if the drug is administered.

45. The method of claim 41 wherein the withdrawal information includes a calculated earliest release date for the animal.

46. The method of claim 40 including alerting the operator if the drug treatment being administered will affect the release date of the animal.

47. The method of claim 40 wherein providing through the computer to an operator at the animal's location drug withdrawal information includes displaying the drug withdrawal period.

48. The method of claim 40 including entering an animal weight and, following entry of the selected drug treatment, providing through the computer to the operator at the drug treatment location a weight-dependent dosage.

49. The method of claim 48 wherein entering into the computer the identity of an animal to be treated includes electronically identifying the animal to the computer.

50. A method of providing drug treatment to a group of animals at a drug treatment location, the method comprising:
    entering into a computer the identity of animals in the group to be treated;
    storing in the computer a list of available drug processing orders and their drug withdrawal periods;
    providing through the computer to an operator a list of available processing orders;
    selecting a drug processing order for the animals from the list of processing orders;
    administering the selected processing order to the animals;
    storing the administered processing order in the computer as an addition to each animal's drug treatment history;
    following administration of the selected processing order and prior to shipment, providing to an operator through the computer withdrawal information that includes or is derived from a drug withdrawal period; and
    decreasing inventory in the computer by the quantity of drugs used in administering the processing order.

51. The method of claim 50 wherein the withdrawal information is a drug withdrawal period.

52. The method of claim 50 wherein the withdrawal information includes an animal shipping date and animal treatment date.

53. The method of claim 50 wherein the withdrawal information includes a calculated earliest release date for the animal.

54. The method of claim 50 including:
    entering a weight for an animal; and
    alerting the operator if the weight is outside an allowable range.

55. The method of claim 50 wherein entering into a computer the identity of animals in the group to be treated includes entering into the computer a group identification number.

56. The method of claim 50 wherein entering into a computer the identity of animals in the group to be treated includes entering into the computer an individual animal identification number.

57. The method of claim 56 including entering an animal weight and, following entry of the selected drug treatment, providing through the computer to the operator a weight-dependent dosage.

58. The method of claim 57 including entering into a computer the identity of animals in the group to be treated includes electronically identifying the animal to the computer.

59. The method of claim 50 including providing through the computer a list of animals and associated shipping status based on the drug withdrawal information.

60. The method of claim 50 including also assisting an operator in selecting and deciding whether to administer a selected drug treatment to an individual animal in the group by:
    storing in a computer health and drug treatment histories of animals to be treated;
    removing each animal to be individually treated from the group of animals;
    entering into the computer at a drug treatment location the identity of each animal to be individually treated;
    in response to entry of the animal's identity, providing through the computer at the drug treatment location the animal's health and drug treatment history, the history including prior diagnoses and drug treatments;
    diagnosing the animal to be treated;
    entering the diagnosis into the computer;
    storing the diagnosis in the computer as an addition to the animal's health history;
    evaluating the animal's health and drug treatment history and the animal's diagnosis;
    storing in the computer a list of available drug treatments;
    providing through the computer to an operator at the drug treatment location a list of available drug treatments;
    based at least in part on the evaluation of the animal's health and drug treatment history and the animal's diagnosis, the operator selecting a drug treatment for the animal from the list of drug treatments;
    entering the selected drug treatment into the computer;
    if desired, administering the selected drug treatment to the animal;
    storing any administered drug treatment in the computer as an addition to the animal's drug treatment history;
    decreasing inventory in the computer by the quantity of drugs used, if any, in administering the drug treatment; and
    entering the animal's weight and, following entry of any selected drug treatment, providing through the computer to the operator a weight-dependent dosage.

61. The method of claim 60 including:
    storing in the computer drug withdrawal periods for the list of available drug treatments;
    following entry of the selected drug treatment, providing through the computer to the operator at the drug treatment location drug withdrawal information that includes or is derived from a drug withdrawal period; and
    the operator determining from the drug withdrawal information whether to administer the drug treatment.

62. The method of claim 61 including alerting the operator if the drug treatment being administered will affect the release date of the animal.

63. The method of claim 62 wherein alerting an operator with withdrawal information includes displaying the drug withdrawal period.

64. The method of claim 61 wherein the withdrawal information in the computer includes the number of days the animal will be late for shipping if the drug is administered.

65. The method of claim 61 wherein providing through the computer at the drug treatment location withdrawal information for the selected drug treatment includes displaying number of days the animal will be late for shipping if the drug is administered and prompting an operator to determine if the operator wants to give the drug treatment.

66. The method of claim 61 wherein providing through the computer at the drug treatment location withdrawal information for the selected drug treatment includes calculating in the computer when the animal may be released.

67. The method of claim 61 wherein providing through the computer at the drug treatment location withdrawal information for the selected drug treatment includes calculating the computer an earliest permitted release date related to a drug withdrawal period and comparing that date with a date the animal is scheduled to be shipped.

68. The method of claim 61 including alerting the operator if the release date is later than the shipping date.

69. The method of claim 61 wherein said providing through the computer at the drug treatment location, the animal's drug treatment history includes providing prior drug treatments administered between two given dates.

70. The method of claim 61 including indicating whether a group of animals is safe to ship based on drug withdrawal information for animals within the group.

71. The method of claim 61 including, in response to entry of the selected drug treatment, alerting the operator through the computer if an entered dosage is outside an allowable range.

72. The method of claim 61 including entering into the computer a destination for the animal after its treatment.

73. The method of claim 61 including alerting an operator, after the entering of the selected drug treatment into the computer, whether the selected drug treatment is invalid.

74. The method of claim 61 wherein entering into the computer the identity of an animal to be treated at the drug treatment location includes electronically identifying the animal to the computer.

75. The method of claim 50 wherein the list of available processing orders is provided to the operator at the drug treatment location.

76. The method of claim 50 wherein the method includes assisting an operator in selecting and deciding whether to administer a particular drug treatment to an individual animal from the group of animals, and the method further comprises:

storing in the computer health and drug treatment histories of individual animals to be treated;

entering into the computer the identity of an animal to be treated individually at the drug treatment location;

in response to entry of the animal's identity, providing through the computer at the drug treatment location the animal's health and drug treatment history, the history including prior diagnoses and drug treatments;

diagnosing the animal to be treated;

entering the diagnosis into the computer;

storing the diagnosis in the computer as an addition to the animal's health history;

evaluating the animal's health and drug treatment history and the animal's diagnosis;

storing in the computer a list of available drug treatments and their drug withdrawal periods;

providing through the computer to an operator at the drug treatment location a list of available drug treatments;

based at least in part on the evaluation of the animal's health and drug treatment history and the animal's diagnosis, the operator selecting a drug treatment for the animal from the list of drug treatments;

entering the selected drug treatment into the computer;

entering the animal's weight and, following entry of the selected drug treatment, providing through the computer to the operator at the drug treatment location a weight-dependent dosage;

if desired, administering the selected drug treatment to the animal;

storing any administered drug treatment in the computer as an addition to the animal's drug treatment history; and decreasing inventory in the computer by the quantity of any administered drug treatment.

77. The method of claim 76 wherein any selected drug treatment administered to the individual animal is administered at the drug treatment location.

78. The method of claim 76 wherein any individual animal drug treatment is administered to the animal at the drug treatment location while the group of animals is at the drug treatment location for administration of the processing order.

79. The method of claim 76 wherein the identity of an animal to be treated individually at the drug treatment location is entered electronically into the computer.

80. The method of claim 79 wherein prior to shipment of an individually treated animal, providing to an operator through the computer drug withdrawal information for the drug treatment administered to the individual animal; and the operator determining from the drug withdrawal information for the administered drug treatment, whether the animal is safe to ship.

81. The method of claim 76 wherein prior to shipment of an individually treated animal, providing to an operator through the computer drug withdrawal information for the drug treatment administered to the individual animal; and the operator determining from the drug withdrawal information for the administered drug treatment, whether the animal is safe to ship.

82. The method of claim 81 wherein any selected drug treatment administered to the individual animal is administered at the drug treatment location.

83. The method of claim 50 wherein the list of available processing orders is provided through the computer to an operator at the treatment location.

84. The method of claim 50 wherein the processing order is administered to the animals at the treatment location by the operator upon selection of the processing order.

85. The method of claim 50 wherein, prior to shipment, the operator determines from the drug withdrawal information whether the group of animals is safe to ship.

86. The method of claim 50 wherein the method includes assisting an operator in selecting and deciding whether to administer a particular drug treatment to an individual animal from the group of animals at the treatment location, and the method further comprises:

storing in the computer health and drug treatment histories of individual animals in the group of animals;

entering into the computer the identity of an animal from the group to be treated individually;

in response to entry of the animal's identity, providing through the computer the animal's health and drug treatment history, the history including prior diagnoses and treatments;

diagnosing the animal to be treated;

entering the diagnosis into the computer;

storing the diagnosis in the computer as an addition to the animal's health history;

evaluating the animal's health and drug treatment history and the animal's diagnosis;

storing in the computer a list of available drug treatments and their drug withdrawal periods;

providing through the computer to an operator a list of available drug treatments;

based at least in part on the evaluation of the animal's health and drug treatment history and the animal's diagnosis, the operator selecting a drug treatment for the animal from the list of drug treatments;

entering the selected drug treatment into the computer;

following entry of the selected drug treatment, providing through the computer to the operator withdrawal information that includes or is derived from a drug withdrawal period;

the operator determining from the drug withdrawal information whether to administer the drug treatment;

if desired, administering the selected drug treatment to the animal;

storing any administered drug treatment in the computer as an addition to the animal's drug treatment history; and decreasing inventory in the computer by the quantity of any administered drug treatment.

87. The method of claim 86 including:

entering the animal's weight and, following entry of the selected drug treatment for the individual animal, providing through the computer to the operator a weight-dependent dosage; and in response to entry of a lot number, pin number, or an estimated shipping date for the animal, indicating whether the animal is safe to ship based on the drug withdrawal information for animals within the group.

88. The method of claim 86 wherein the list of available drug treatments is provided through the computer to an operator at the drug treatment location.

89. The method of claim 86 wherein the drug withdrawal information provided through the computer to the operator is provided to the operator at the drug treatment location.

90. The method of claim 86 wherein the list of available drug treatments and the drug withdrawal information that includes or is derived from a drug withdrawal period are provided to an operator at the drug treatment location.

91. The method of claim 86 wherein any selected drug treatment administered to the animal is administered at the drug treatment location.

92. The method of claim 86 wherein the list of available drug treatments, the drug withdrawal information, and any drug treatment administered to the animal are provided at the drug treatment location.

93. The method of claim 92 wherein any drug treatment administered to the animal is administered while the group of animals is at the drug treatment location.

94. The method of claim 86 wherein the identity of an animal to be treated is entered electronically into the computer.

95. The method of claim 50 wherein the drug withdrawal information provided to the operator through the computer prior to shipment of the animal is provided to the operator at the drug treatment location.

96. A method of assisting an operator in selecting and deciding whether to administer a selected drug treatment to animals which are selected from a group of retained animals for treatment at a drug treatment location, the method comprising:

storing in a computer health and drug treatment histories of animals to be treated;

entering electronically into the computer the identity of an animal to be treated at the drug treatment location;

in response to entry of the animal's identity, providing through the computer at the drug treatment location the animal's health and drug treatment history, the history including prior diagnoses and drug treatments;

diagnosing the animal to be treated;

entering the diagnosis into the computer;

storing the diagnosis in the computer as an addition to the animal's health history;

evaluating the animal's health and drug treatment history and the animal's diagnosis;

storing in the computer a list of available drug treatments and their drug withdrawal periods;

providing through the computer to an operator at the drug treatment location a list of available drug treatments;

based at least in part on the evaluation of the animal's health and drug treatment history and the animal's diagnosis, the operator selecting a drug treatment for the animal from the list of drug treatments;

entering the selected drug treatment into the computer;

following entry of the selected drug treatment, providing through the computer to the operator at the drug treatment location drug withdrawal information that includes or is derived from a drug withdrawal period;

the operator determining from the drug withdrawal information whether to administer the drug treatment;

if desired, administering the selected drug treatment to the animal;

storing any administered drug treatment in the computer as an addition to the animal's drug treatment history; and decreasing inventory in the computer by the quantity of any administered drug treatment.

97. The method of claim 96 including:

entering an animal weight and, following entry of the selected drug treatment, providing through the computer to the operator at the drug treatment location a weight-dependent dosage; and in response to entry of a lot number, pen number, or an estimated shipping date for the animal, indicating whether the animal is safe to ship based on the drug withdrawal information for animals within the group.

98. A method of providing drug treatment to a group of animals at a drug treatment location and in assisting an operator in selecting and deciding whether to administer a particular drug treatment to an individual animal at the location, the method comprising:

entering electronically into a computer the identity of animals in the group to be treated;

storing in the computer a list of available processing orders and their drug withdrawal periods;

providing through the computer to an operator a list of available processing orders;

selecting a drug treatment for the animals from the list of processing orders;

entering the selected processing order into the computer;

administering the processing order to the animals;

storing the administered processing order in the computer as an addition to each animal's drug treatment history;

decreasing inventory in the computer by the quantity of the administered processing order;

storing in the computer health and drug treatment histories of animals to be treated;

entering electronically into the computer the identity of an animal to be treated individually at the drug treatment location;

in response to entry of the animal's identity, providing through the computer at the drug treatment location the animal's health and drug treatment history, the history including prior diagnoses and drug treatments;

diagnosing the animal to be treated;

entering the diagnosis into the computer;

storing the diagnosis in the computer as an addition to the animal's health history;

evaluating the animal's health and drug treatment history and the animal's diagnosis;

storing in the computer a list of available drug treatments and their drug withdrawal periods;

providing through the computer to an operator at the drug treatment location a list of available drug treatments;

based at least in part on the evaluation of the animal's health and drug treatment history and the animal's diagnosis, the operator selecting a drug treatment for the animal from the list of drug treatments;

entering the selected drug treatment into the computer;

entering the animal's weight and, following entry of the selected drug treatment, providing through the computer to the operator at the drug treatment location a weight-dependent dosage;

if desired, administering the selected drug treatment to the animal;

storing any administered drug treatment in the computer as an addition to the animal's drug treatment history;

decreasing inventory in the computer by the quantity of any administered drug treatment;

prior to shipment of the animal, providing to an operator through the computer drug withdrawal information; and the operator determining from the drug withdrawal information whether the animal is safe to ship.

99. The method of claim 98 wherein the list of available processing orders is provided to the operator at the drug treatment location.

100. The method of claim 98 wherein the processing order is administered to the animals at the treatment location by the operator upon selection of the processing order.

101. The method of claim 98 wherein the list of available processing orders is provided to an operator at the drug treatment location.

102. The method of claim 101 wherein the processing order is administered to the group of animals at the drug treatment location.

103. The method of claim 98 wherein an individual animal to be treated is diagnosed at the drug treatment location while the group of animals is at the drug treatment location.

104. The method of claim 98 wherein the selected drug treatment to be administered to an individual animal, if administered, is administered at the drug treatment location.

105. The method of claim 98 wherein the drug withdrawal information provided to the operator prior to shipment of the animal is provided to the operator at the treatment location.

* * * * *